(12) United States Patent
Nihart

(10) Patent No.: US 9,597,279 B2
(45) Date of Patent: Mar. 21, 2017

(54) ANTI-AGING DERMAL COMPOSITION COMPRISING HERBAL EXTRACTS

(71) Applicant: HDDC Holdings, LLC, Poway, CA (US)

(72) Inventor: Troy Nihart, Temecula, CA (US)

(73) Assignee: HDDC HOLDINGS, LLC, Poway, CA (US)

( * ) Notice: Subject to any disclaimer, the term of this patent is extended or adjusted under 35 U.S.C. 154(b) by 263 days.

(21) Appl. No.: 14/631,434

(22) Filed: Feb. 25, 2015

(65) Prior Publication Data

US 2015/0245991 A1 Sep. 3, 2015

Related U.S. Application Data

(60) Provisional application No. 61/946,508, filed on Feb. 28, 2014.

(51) Int. Cl.

| | |
|---|---|
| *A01N 65/00* | (2009.01) |
| *A61K 8/97* | (2006.01) |
| *A61K 8/37* | (2006.01) |
| *A61K 8/34* | (2006.01) |
| *A61K 8/73* | (2006.01) |
| *A61K 8/67* | (2006.01) |
| *A61Q 19/08* | (2006.01) |
| *A61K 8/362* | (2006.01) |
| *A61K 8/92* | (2006.01) |
| *A61Q 19/10* | (2006.01) |

(52) U.S. Cl.
CPC ............... *A61K 8/97* (2013.01); *A61K 8/342* (2013.01); *A61K 8/345* (2013.01); *A61K 8/362* (2013.01); *A61K 8/375* (2013.01); *A61K 8/678* (2013.01); *A61K 8/73* (2013.01); *A61K 8/731* (2013.01); *A61K 8/735* (2013.01); *A61K 8/922* (2013.01); *A61Q 19/08* (2013.01); *A61K 2800/524* (2013.01); *A61Q 19/10* (2013.01)

(58) Field of Classification Search
CPC ....................................................... A61K 36/00
USPC .......................................................... 424/725
See application file for complete search history.

(56) References Cited

U.S. PATENT DOCUMENTS

| | | | |
|---|---|---|---|
| 7,807,711 B2 | 10/2010 | Korthout et al. | |
| 8,293,786 B2 | 10/2012 | Stinchcomb et al. | |
| 8,435,556 B2 | 5/2013 | Stinchcomb et al. | |

OTHER PUBLICATIONS

G.O. Burr and M.M. Burr, On the Nature and Role of the Fatty Acids Essential in Nutrition, J. Biol. Chem. 1930 86, 587-621.
E. Small, Advances in medicinal plant research 2007, 2007, pp. 1-39.
James Geiwitz, THC in Hemp Foods and Cosmetics: The Appropriate Risk Assessment, 2001.
Vito Mediavilla and Simon Steinemann, Essential Oil of Cannabis Sativa L. Strains, Swiss Federal Research Station for Agroecology and Agriculture.
Johannes Novak, Karin Zitterl-Eglseer, Stanly G. Deans, and Chlodwig M. Franz, Essential Oils of Different Cultivars of Cannabis sativa L. and their anti-microbial activity, 2001.

*Primary Examiner* — Michael Meller
(74) *Attorney, Agent, or Firm* — Procopio, Cory, Hargreaves & Savitch LLP; Lisel Maria Ferguson

(57) ABSTRACT

This application discloses an anti-aging composition for dermal application comprising cannabidiol hemp oil, chuanxiong extract, mondo grass extract, Chinese foxglove extract, female and *panax ginseng* extract, dragon's blood resin, lilyturf root, and jojoba oil. Other active ingredients may include licorice root, *Astragalus membranceus*, tree peony, mulberry bark extraction, longan fruit, wild pansy, rose *canina* seed powder, and Radix polygoni multiflori. The composition is formulated with other components to serve as a cleanser, a moisturizer, a serum, a gel masque, an eye cream, a toner, or an exfoliant.

19 Claims, No Drawings

ANTI-AGING DERMAL COMPOSITION COMPRISING HERBAL EXTRACTS

CROSS REFERENCE TO RELATED APPLICATIONS

This application claims the benefit under 35 U.S.C. §119 (e) of U.S. Provisional Application No. 61/946,508, filed Feb. 28, 2014.

FIELD OF THE INVENTION

The present invention relates to cosmetic products, namely, anti-aging compositions for dermal application. The composition comprises various herbal extracts and vegetable oil, in particular *Cannabis sativa* oil with cannabidiol, and dragon's blood resin. The anti-aging composition may be used as a cleanser to clean facial skin, as an eye cream to reduce the fine crow's lines, as a gel masque to massage and sooth aging skin, as a serum or moisturizer to moisturize dry skin, or as an exfoliant to remove dead skin cells.

BACKGROUND OF THE INVENTION

Aging is an inevitable progression of life. However, with the advance of anti-aging medicine and science, certain aging signs may be lessened or delayed. In the U.S., the population is aging, with more than 10% of the population now 65 years of age or older. This percentage is set to increase as the "baby boomer" generation enters retirement.

Aging is a multi-factor process. Oxidative stress is recognized as a primary cause in aging. Oxidative stress reflects an imbalance between the systemic manifestation of reactive oxygen species and a biological system's ability to readily detoxify the reactive intermediates or to repair the resulting damage. When there is an imbalance of the normal redox state of cells, excessive presence of peroxides and free radicals may damage all components of cells.

The anti-aging market is forecasted to reach $290 billion by 2015. Anti-aging products come in a variety of forms, with skin care products, which seek to eliminate the most prominent and visible signs of age, as the most popular line of products. In this market, herb-based, natural products are strongly favored. However, marketing of these products does face skepticism and conflicting clinical research results.

In the anti-aging skin care area, skin firming, reduction of "crow's feet," skin moisturizing, and discoloration reduction are desirable effects. Various ingredients derived naturally or synthetically are sought for their ability to achieve the above effects. Most ingredients known for their anti-oxidant properties are beneficial in the anti-aging industry. In particular, retinoids, forms of vitamin A, are useful in skin firming.

Vitamin A regulates keratinization to improve skin's texture, firmness, and smoothness. Vitamin A esters convert to retinoic acid and provide anti-aging, anti-oxidant benefits. Retinoic acids provide these benefits by stimulating production of epidermal protein, which increases skin thickness and elasticity.

Hyaluronic acid is another popular component in the anti-aging cosmetic industry. Hyaluronic acid may be found in the dermis skin layer and is responsible for moisturizing and firming the skin. When used on the skin, hyaluronic acid acts to hold moisture to the skin's surface. For dry and aging skin, moisture retention is crucial in giving the skin a young, firm appearance.

While various anti-aging cosmetic products are available, certain components used in anti-aging cosmetics have inherent limitations. Tretinoin, a carboxylic acid form of vitamin A, is shown to reduce wrinkles but also has many side effects. While treating photoaging in skin by increasing production of mast cells in the dermis, tretinoin may cause redness, scaling, itching, and burning in sensitive subjects. This is due to its high acidity.

Other anti-aging cosmetic products may contain mineral oil and petrolatum. While petrolatum is popular in skin care as it hastens skin healing and retains moisture on the skin's surface, it also is greasy and does not contribute to skin firming. Mineral oil is similar to petrolatum in its origin. Apart from retaining some moisture, mineral oil does little by way of anti-aging properties.

Polyunsaturated fatty acids (omega-6 and omega-3) are essential to skin health. Metabolism of linoleic acid and alpha-linoleic acid is limited in the skin. Topical and oral supplementations of essential fatty acids are effective means to supply these essential fatty acids to the skin. Some anti-aging cosmetic products do not include these important polyunsaturated fatty acids.

Essential fatty acids (EFAs) found in hemp oil act as moisturizers to trap moisture on the skin. Moreover, the fatty acids ratio in hemp oil closely matches the human skin composition and body, which is 3:1 ratio of omega-6 to omega-3 essential fatty acids. EFAs are proven to play a preventive role in skin aging and a healthy moisture balance for the skin.

Omega fatty acids are a group of unsaturated fatty acids considered to be important to physiological development in mammals. In particular, omega-3 fatty acids are considered to be vital for normal metabolism. These fatty acids receive their names based on the location of the first double bond from the tail end (omega end) of the carbon chain.

Omega-3 fatty acids are a group of three (3) fatty acids called α-linolenic acid (ALA), eicosapentaenoic acid (EPA), and docosahexaenoic acid (DHA). Mammals have limited ability to synthesize omega-3 fatty acids. Given their importance in metabolism, mammals must consume omega-3 fatty acids to ensure normal metabolism.

Omega-6 fatty acids are a family of unsaturated fatty acids that have in common a carbon-carbon double bond in the n-6 position. Omega-6 fatty acids are considered to be important to a mammal's diet. The relative ratio of omega-6 to omega-3 fatty acids in Western diet is about 10:1 and up to 30:1. An excessive ratio of omega-6 to omega-3 fatty acids may interfere with omega-3 activity, storage, and conversion to eicosanoid precursors.

The role of fatty acids in skin health is prominent. In a series of studies, George and Mildred Burr determined that rats consuming a no-fat diet developed visible skin abnormalities and heightened water loss on skin. In humans, skin abnormalities and transdermal water loss are observed with essential fatty acid deficiency.

Plants in the *cannabis* genus include *Cannabis sativa, Cannabis ruderalis*, and *Cannabis* indicia. In Asia, *cannabis* plants have long been used for medicinal purposes. Hemp (*Cannabis sativa* L.) is a plant with many industrial applications including fiber, oil, fabric, paper, and construction materials.

In the West, *cannabis* is mainly cultivated for recreational uses. Consequently, most *cannabis* plants in the West are $\Delta^9$-tetrahydrocannabinol (THC)-rich. Hemp, on the other hand, is not rich in THC. Hemp finished products are imported and sold legally in the United States because of this. Hemp products sold in the United States include fiber, jewelry, hemp oil, hemp protein, hemp seeds, and other products derived from the hemp plant.

Hemp oil is produced by cold pressing of hemp seeds and hemp plant materials. Hemp seed is the seed of the plant *Cannabis sativa* L., which contains only trace amounts of THC. The mature stalk of the hemp plant may also be cold pressed for hemp oil. Hemp oil contains a ratio of approximately 3:1, omega-6 fatty acids:omega-3 fatty acids. Hemp oil is sold legally in the United States and usually contains less than 10 ppm of THC.

Cannabinoids are a family of compounds found in the *cannabis* plant. The prominent compounds among the cannabinoids are $\Delta^9$-tetrahydrocannabinol (THC), cannabidiol (CBD), cannabichromene (CBC), cannabigerol (CBG), cannabidivarin (CBDV), among other compounds. There are up to eighty five (85) known compounds in the cannabinoid family. While THC is known for its psychoactive characteristics, other cannabinoids such as CBD and CBC are not psychoactive.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. CBD is a natural constituent in hemp plants, as well as other plants in the *cannabis* genus. However, the CBD concentration in each *cannabis* plant depends on the strain.

Cannabidiol may be applied to healthy human volunteers at high doses, up to 700 mg/day, for a long period of time without toxicity or serious side effects (Consroe et al., Pharmacol. Biochem. Behav. 40:701-708, 1991; Cunha et al., Pharmacology 21:175-185, 1980).

U.S. Pat. No. 6,630,507 describes the use of cannabinoids, in particular cannabidiol, for the treatment of diseases associated with oxidative stress. Oxidative stress-associated diseases refer to pathological conditions that result at least in part from the production of or exposure to free radicals, particularly oxyradicals, or reactive oxygen species. The application of a free radical inhibitor, scavenger, or catalyst may provide detectable benefits by decreasing symptoms, increasing survival rate, or providing other detectable clinical benefits in treating or preventing the oxidative stress-associated diseases.

Cannabinoids in the above invention are reported to have antioxidant properties. Antioxidants act by scavenging biologically important reactive free radicals or other reactive oxygen species, or by preventing their formation, or by catalytically converting the free radicals or other reactive oxygen species to a less reactive species.

The combination of cannabinoids from natural sources and other components having anti-oxidative properties may give anti-aging results when used on human skin. The following invention aims to provide anti-aging cosmetic formulations with anti-oxidative properties from cannabinoids.

Abbreviations

ALA: α-linolenic acid
CBD: Cannabidiol
CBC: Cannabichromene
CBG: Cannabigerol
CBDV: Cannabidivarin
DHA: Docosahexaenoic acid
EFA: Essential Fatty Acids
EPA: Eicosapentaenoic acid
FDA: Food and Drug Administration
GRAS: General Recognized as Safe
INCI: International Nomenclature of Cosmetic Ingredients
IUPAC: International Union of Pure and Applied Chemistry
qs: quantity sufficient
THC: Tetrahydrocannabinols
THSG: 2,3,5,4'-tetrahydroxystilbene-2-O-beta-D-glucoside
wt/wt: weight/weight

DETAILED DESCRIPTION OF THE INVENTION

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean that items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoids" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol, (−)-(3S,4S)-7-hydroxy-delta-6-tetrahydrocannabinol-1,1-dimethylheptyl, (+)-(3S,4S)-7-hydroxy-$\Delta$-6-tetrahydrocannabinol, and $\Delta^8$-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendiol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained by cold-pressing industrial hemp with trace amounts of THC. Cannabidiol in this present invention is provided as a natural constituent of hemp oil.

The anti-aging dermal composition described herein comprises of various herb extracts selected to target different issues in skin aging, such as photo-damage, oxidative stress damage, dryness, and skin sagging. Depending on the specific formulation, the anti-aging dermal composition may be used as an eye cream, an exfoliant, a serum, a gel masque, a moisturizer, a toner, or a cleanser. The anti-aging dermal composition may be applied at least twice daily on the skin to obtain results, such as moisturizing, reduced wrinkles, reduced skin pigmentation, and reduced acne.

In a preferred embodiment, the dermal composition is a cleanser and contains a base. The base provides the preferred environment for the active ingredients. The cleanser base preferably comprises the following ingredients in sufficient quantities: de-ionized water, candellila/jojoba/rice bran polyglyceryl-3-esters, bentonite clay, glyceryl stearate (palm, grape seed, and sunflower), cetearyl alcohol (coconut and palm kernel), kaolin clay, sodium stearoyl lactylate (vegetable derived), glycerin (plant source), cetyl hydroxyethylcellulose (plant cellulose thickener), xanthan gum (fermented sugar), caprylyl glycol, potassium sorbate, tocopheryl acetate & tocopherol (vitamin E). This base is suitable for the cleanser.

In another preferred embodiment, the dermal composition is used as an eye cream and contains a base. The cream base for the eye cream comprises the following ingredients: de-ionized water, candellila/jojoba/rice bran polyglyceryl-3-esters, glyceryl stearate (palm, grape seed, and sunflower), cetearyl alcohol (coconut and palm kernel), sodium stearoyl lactylate (vegetable derived), glycerin (plant source), cetyl hydroxyethylcellulose (plant cellulose thickener), xanthan gum (fermented sugar), caprylyl glycol, potassium sorbate, tocopheryl acetate & tocopherol (vitamin E).

In another preferred embodiment, the dermal composition is used as a serum. The serum base for the serum comprises the following ingredients: aloe vera, glycerin (plant source), caprylyl glycol, potassium sorbate, hyaluronic acid (sodium hyaluronate), xanthan gum (fermented sugar), tocopheryl acetate and tocopherol (vitamin E). This base gives the serum an overall liquid body, enabling faster absorption when rubbed onto the skin.

In yet another preferred embodiment, the dermal composition is used as an exfoliant. The exfoliant base comprises the following ingredients in sufficient quantities: de-ionized water, candellia/jojoba/rice bran polyglyceryl 3-esters, bentonite clay, glyceryl stearate (palm, grape seed, and sunflower), cetearyl alcohol (coconut and palm kernel), kaolin clay, sodium stearoyl lactylate (vegetable derived), glycerin (plant sources), cetyl hydroxyethylcellulose, xanthan gum, caprylyl glycol, potassium sorbate, tocopherol acetate and tocopherol.

In another preferred embodiment, the dermal composition is used as a gel masque. The gel masque base comprises the following ingredients in sufficient quantities: de-ionized water, glycerin (plant source), caprylyl glycol, xanthan gum (in keltrol solution), and potassium sorbate.

In yet another preferred embodiment, the dermal composition is used as a moisturizer. The moisturizer base comprises the following ingredients in sufficient quantities: de-ionized water, candellia/jojoba/rice bran polyglyceryl 3-esters, glyceryl stearate (palm, grape seed, and sunflower), cetearyl alcohol (coconut and palm kernel), sodium stearoyl lactylate (vegetable derived), glycerin (plant sources), sodium hyaluronate, cetyl hydroxyethylcellulose, xanthan gum, caprylyl glycol, potassium sorbate, tocopherol acetate and tocopherol.

The preferred embodiment may contain wound-healing ingredients, such as *Croton lechlerin* resin, or dragon's blood resin, at between about 0.1% (wt/wt) and about 3.5% (wt/wt). *Panax ginseng* extract is another skin healing ingredient that may be used in this composition at between about 0.1% (wt/wt) and about 4% (wt/wt). *Croton lechleri* resin and *Panax ginseng* extract may be obtained on the market. *Croton lechleri* resin should be in liquid form for mixing.

The preferred embodiment may contain jojoba oil as a natural fungicide to preserve the composition at between about 1% (wt/wt) to about 3% (wt/wt). Jojoba oil is a slight yellow liquid produced in the seed of the *Simmondsia chinensis* plant, with high stability. Jojoba oil acts as a fungicide and jojoba polyclyceryl-3-ester acts as a bulking agent.

The anti-oxidant ingredients include *Angelica sinensis* (dong quai or female *ginseng*) at between about 0.1% (wt/wt) and about 2% (wt/wt), *Ligusticum wallichii* at between about 0.1% (wt/wt) and about 3% (wt/wt), *Rehmannia chinesis* (Chinese foxglove) at between about 0.1% (wt/wt) and about 4% (wt/wt), *Paeonia albiflora* (white peony) or *Paeonia suffruticosa*) at between about 0.1% (wt/wt) and about 4% (wt/wt), and *Panax ginseng* at between about 0.1% (wt/wt) and about 4% (wt/wt). *Angelica sinesis* may have an anti-coagulant effect that may be countered with *Artemisia vulgaris* if required. *Ligusticum wallichii* is used in traditional Chinese medicine for disorders such as ichemia and thrombosis, which are oxidative stress disorders. *Ligusticum wallichii* is also a source of ferulic acid, which is a phenolic compound. *Rehmannia chinesis* has anti-inflammatory properties. *Paeonia albiflora* or *Paeonia suffruticosa* root extract accelerates the wound healing process by decreasing the surface area of the wound.

The hyaluronic acid ingredient includes sodium hyaluronic in small molecular weight. Hyaluronic acid is non-sulfated glycosaminoglycan, which is a chief component of the extracellular matrix, and contributes significantly to cell proliferation and migration. Small molecular weight hyaluronic acid is preferred in skin care for better penetration, hence sodium hyaluronic is selected. Sodium hyaluronate is present at between about 0.5% (wt/wt) to about 2% (wt/wt).

The moisturizing and omega fatty acid ingredients include hemp oil, sunflower oil, and *Rehmannia chinesis* (Chinese foxgloves) extracts. Hemp is grown organically and cold pressed for oil. Sunflower oil is cold pressed from sunflower seed. *Rehmannia chinesis* extract has skin-conditioning properties. Hemp oil and sunflower oil are moisturizers and provide EFAs to the skin.

The sodium hydroxide ingredient is present to increase the pH level in the overall composition and to prevent the dragon's blood resin from turning a shade of pink. A slightly basic or neutral pH environment prevents the composition from being abrasive to the skin.

The coagulant ingredient is *Artemisia vulagris*, or mugwort. Mugwort is commonly used in medicine in both the East and the West. Mugwort may counter any anti-coagulant effect that *Angelica sinensis* may have. Mugwort extract is also a skin conditioning solution. *Astragalus membraneceus* extract is present at between about 0.1% (wt/wt) and about 2% (wt/wt).

The dermal composition may further comprise *Ophiopogon japonicus* (mondo grass) at between about 0.1% (wt/wt) and about 3% (wt/wt), which is beneficial in the moisturizing of membranes. When used on skin, mondo grass extracts act to moisturize the skin.

*Dimocarpus longan* fruit contains gallic acid, ellagic acid, and corilagin acid, which are phenolic acids with anti-oxidative properties. Longan fruit extract also inhibits tyrosinase activity. As tyrosinase activity oxidizes phenol compounds, a reduction in tyrosinase activity also reduces oxidation. Tyrosinase also affects melanin synthesis. In tyrosinase activity, more melanin is produced, resulting in changed in skin pigmentation. A reduction of tyrosinase activity therefore may reduce skin pigmentation and slow or reverse skin aging appearance. *Dimocarpus longan* fruit extract is present at between about 0.1% (wt/wt) and about 2.5% (wt/wt).

Radix polygoni multiflori is an herb used in Chinese medicine to treat graying and skin pigmentation due to age. Its active ingredient is 2,3,5,4'-tetrahydroxystilbene-2-O-beta-D-glucoside (THSG), which is shown to inhibit melanogenesis, the process of skin pigmentation. The dermal composition may comprise this ingredient to prevent skin pigmentation. Radix polygoni multiflori extract is present at between about 0.1% (wt/wt) and about 3% (wt/wt).

In another preferred embodiment, the dermal composition may further comprise *Glycyrrhiza glabra* (licorice) extract. Licorice extract reduces acidity of the composition as a whole. Licorice also acts to reduce ulcers in membranes and has skin conditioning properties. *Glycyrrhiza glabra* extract is present at between about 0.1% (wt/wt) and about 2% (wt/wt).

The dermal composition may further comprise *Astragalus membraneceus* extract, which is anti-inflammatory and speeds wound healing. For the skin, *Astragalus membraneceus* is beneficial as protection against sun-damage. *Astragalus membraneceus* extract is present at between about 0.1% (wt/wt) and about 2% (wt/wt).

The anti-oxidant ingredients in the serum are cannabinoids, in particular cannabidiol, as natural constituents of *Cannabis sativa* L., *Paeonia suffruticosa* bark extract, *Schisandra chinensis*, and *Morus alba* extract. Cannabinoids may be used to treat oxidative stress related diseases and conditions, of which aging is one. *Paeonia suffruticosa* extract exhibits high free radical scavenging capacity, ion-chelating ability, reducing power, and inhibition of lipid peroxidation. *Morus alba*, or white mulberry, has anti-oxidant properties. *Schisandra chinensis* extract contains the anti-oxidant schizandrin.

*Viola tricolor*, known also as wild pansy extract, is anti-inflammatory and anti-microbial due to its cyclotides content. The anti-aging composition may further comprise *Viola tricolor* extract for preservation and anti-inflammatory purposes. *Viola tricolor* extract is present at between about 0.1% (wt/wt) and about 4% (wt/wt).

*Rosa canina* powder is the dry form of rose hip, which is harvested from the plant *Rosa canina*. *Rosa canina* powder contains a high vitamin C content and lycopene, a strong anti-oxidant. Lycopene prevents oxidation of low density lipoprotein and other cellular membranes. On skin, lycopene prevents the oxidation of skin lipoprotein. *Rosa canina* powder is present in this dermal composition at between about 0.1% (wt/wt) and about 1% (wt/wt).

Green tea extract is the extract from the leaf of the plant *Camellia sinensis*. The anti-oxidative properties of green tea extract are attributed to green tea catechins, namely, epicatechin, epigallocatechin, epicatechin gallate, and epigallocatechin gallate. Used on skin, green tea extract inhibits lipid oxidation, which in turn preserves skin tensile strength. *Camellia sinensis* extract is present at between 0.1% (wt/wt) and about 4% (wt/wt).

For the herbal extracts, ethanol in water may be used for the extraction process. The resulting extracts are in aqueous form and contain water. Herbal extracts as used in the present invention may be obtained on the market, or may be produced in-house using standard extraction methods. Ethanol concentration in the extracts may be reduced to minimize drying properties when used on skin.

All of the above ingredients may be purchased on the market. *Cannabis sativa* L. oil containing cannabinoids may be purchased legally in the United States as hemp oil, which has high EFAs and contains cannabidiol as a natural constituent. It is recommended that the hemp oil used in this embodiment has a cannabinoid, specifically cannabidiol, content between 5% (wt/wt) and 35% (wt/wt).

In each preferred embodiment, the tocopherol and tocopherol derivatives component comprises between about 1% (wt/wt) to about 8% (wt/wt) of the composition.

The dermal composition may further comprise de-ionized water to provide a base for dissolution of the ingredients and to adjust viscosity according to need. Sodium hydroxide solution is used last to adjust pH level of the anti-aging composition to between 6.0 and 8.0.

For each ounce of the cleanser, the preferred formulation contains, in weight percentage:

Between about 0.1% and about 4% of *Cannabis sativa* L. oil containing 20% (wt/wt) of cannabinoids;

Between about 0.1% and about 2% of *Artemisia vulgaris* extract;

Between about 0.1% and about 3% of *Ligusticum wallichii* extract;

Between about 0.1% and about 4% of *Rehmannia chinensis* extract;

Between about 0.1% and about 2% of *Ophiopogon japonicus* extract;

Between about 0.1% and about 2% of *Angelica sinensis* extract;

Between about 0.1% and about 5% of *Panax ginseng* extract;

Between about 0.1% and about 3.5% of *Croton lechleri* resin;

Between about 1% and about 4% of jojoba oil;

Between about 1% and about 6% of tocopherol acetate & tocopherol; and

Between about 1% and about 8% of glycerin.

For each ounce of the serum, the preferred formulation contains, in weight percentage:

Between about 0.1% and about 4% of *Cannabis sativa* L. oil containing about 20% (wt/wt) of cannabidiol;

Between about 0.1% and about 3% of *Panax ginseng* extract;

Between about 0.1% and about 1.5% of *Croton lechleri* extract;

Between about 0.1% and about 2% of *Angelica dahurica* extract;

Between about 0.1% and about 3% of *Glycyrrhiza glabra* extract;

Between about 0.1% and about 2% of *Astragalus membranceus* extract;

Between about 0.1% and about 2% of *Schisandra chinensis* extract;

Between about 0.1% and about 2.5% of *Camellia sinensis* green tea extract;

Between about 0.1% and about 2.5% of *Lycium barbarum* (goji berry) fruit extract;

Between about 0.1% and about 2% of aloe vera oil;

Between about 0.1% and about 2% of tocopherol and tocopherol derivatives; and

Between about 1% and about 8% of glycerin.

For each ounce of the exfoliant solution, the preferred formulation contains, in weight percentage:

Between about 0.1% and about 4% of *Cannabis sativa* L. oil containing about 20% (wt/wt) of cannabidiol;

Between about 0.1% and about 3% of *Glycyrrhiza glabra* extract;

Between about 0.1% and about 2.5% of *Dimocarpus longan* fruit extract;

Between about 0.1% and about 2% of Radix polygoni multiflori extract;

Between about 0.1% and about 3% of *Panax ginseng* extract;

Between about 0.1% and about 4% of *Viola tricolor* extract;

Between about 0.1% and about 3% of *Ligusticum wallichii* extract;

Between about 0.1% and about 2% of *Croton lechleri* extract;

Between 1% and about 3% of jojoba oil;

Between 1% and about 3% of sunflower oil;

Between 1% and about 2% of rose *canina* seed powder; and

Between about 0.1% and about 0.5% of tocopherol or other vitamin E derivatives.

For each ounce of the gel masque, the preferred formulation contains, in weight percentage:

Between about 0.1% and about 5% of *Cannabis sativa* L. oil containing about 20% (wt/wt) of cannabinoids;

Between about 0.1% and about 2% of *Angelica sinensis* root extract;

Between about 0.1% and about 3% of *Astragalus membranceus* extract;

Between about 0.1% and about 2% of *Croton lechleri* extract;

Between about 0.1% and about 2% of *Glycyrrhiza glaba* root;

Between about 0.1% and about 1.5% of *Dimocarpus longan* fruit extract;

Between about 0.1% and about 3% of *Ophiopogon japonicus* root extract;

Between about 0.1% and about 2% of *Lycium barbarum* (goji berry) extract;

Between about 0.1% and about 3% of *Paeonia albiflora* (white peony) extract;

Between about 0.1% and about 4% of *Panax ginseng* extract;

Between about 0.1% and about 2% of *Viola tricolor* (wild pansy) extract;

Between about 0.1% and about 5% of *Ligusticum wallichii* extract;

Between about 2% to about 6% of glycerin; and

Between about 0.1% to about 4% of *Camellia sinensis* (green tea) extract.

For each ounce of the eye cream, the preferred formulation contains, in weight percentage:

Between about 0.1% and about 4% of *Cannabis sativa* L. oil containing about 20% (wt/wt) cannabinoids;

Between about 0.1% and about 3% of *Panax ginseng* extract;

Between about 0.1% and about 2% of *Astragalus membranaceus* extract;

Between about 0.1% and about 2% of *Croton lechleri* resin;

Between about 0.1% and about 3% of *Paeoniae albiflora* extract;

Between about 0.1% and about 3% of *Rehmannia chinesis* extract;

Between about 0.1% and about 2% of *Lycium barbarum* extract;

Between about 0.1% and about 2.5% of Radix polygon multiflori extract;

Between about 0.1% and about 3% of *Ophiopogon japonicus* extract;

Between about 0.1% and about 2% of *Schisandra chinensis* extract;

Between about 0.1% and about 2.5% of jojoba oil;

Between about 0.5% and about 3.5% of sunflower oil;

Between about 1% and about 6% of tocopherol and tocopherol derivatives;

Between about 1% and about 7% of glycerin.

For each ounce of the moisturizer, the preferred formulation contains, in weight percentage:

Between about 0.1% and about 4% of *Cannabis sativa* L. oil containing about 15% (wt/wt) cannabinoids;

Between about 0.1% and about 2.5% of *Panax ginseng* extract;

Between about 0.1% and about 3% of *Glycyrrhiza glabra* root extract;

Between about 0.1% and about 2% of *Astragalus membranaceus* extract;

Between about 0.1% and about 2% of *Croton lechleri* resin;

Between about 0.1% and about 3% of *Paeoniae suffruticosa* extract;

Between about 0.1% and about 2.5% of *Angelica sinensis* extract;

Between about 0.1% and about 2% of *Morus alba* bark extract;

Between about 0.1% and about 2% of *Morus alba* leaf extract;

Between about 1% and about 7% of glycerin;

Between about 1% and about 5% of tocopherol or tocopherol derivatives.

Ingredients are obtained according to the embodiments above. The water phase comprises of de-ionized water, bulking agents, cosmetic fillers, emulsifiers, preservatives, moisturizing agents, and herbal extracts. Ingredients for the water phase are combined and mixed. Water phase ingredients may be separated into different sequences as needed. The oily phase comprises of hemp oil, sunflower oil, jojoba oil, and other oily ingredients. Oily phase ingredients are combined and stirred, with heat application at 50° C. to 70° C. to reduce viscosity and facilitate mixing.

When the water phase and the oily phase are combined, continuous stirring and heat application assist with mixing. Cool the mixture down to room temperature before adjusting the pH with NaOH solution.

The dermal composition according to these preferred embodiment may be applied to the human skin at least twice daily to reduce signs of aging, such as crow's feet, sagging skin, or pigmentation due to age.

EXAMPLES

Example 1

| | | Preferred formulation for a cleanser | |
|---|---|---|---|
| Sequence | Percent | Ingredient | INCI Name |
| 1 | 36.0 | Deionized water | Water |
| 3 | 2.0 | Hemp oil | Hemp oil |
| 2 | 1.0 | *Mugwort* extract | *Artemisia vulgaris* extract |
| 2 | 1.0 | *Ligusticum chuanxiong* extract | *Ligusticum chuanxiong* extract |
| 2 | 1.0 | *Chinese foxglove* extract | *Rehmannia chinesis* root extract |
| 2 | 1.0 | *Lilyturf* root | *Ophiopogon japonicus* root extract |

| \multicolumn{4}{c}{Preferred formulation for a cleanser} |

| Sequence | Percent | Ingredient | INCI Name |
|---|---|---|---|
| 2 | 1.0 | *Dong quai* extract | *Angelica sinensis* root extract |
| 2 | 1.5 | *Panax ginseng* | *Panax ginseng* root extract |
| 2 | 0.5 | Dragon's blood resin | *Croton lechleri* resin extract |
| 3 | 2.0 | *Jojoba* oil unsaponifiables | *Jojoba* oil |
| 4 | 8.0 | Candellila/*jojoba*/rice bran polyglyceryl-3-esters | Candellila/*jojoba*/rice bran polyglyceryl-3-esters |
| 1 | 6.5 | Bentonite clay | Bentonite |
| 4 | 8.0 | Glyceryl stearate | Glyceryl stearate |
| 4 | 6.0 | Cetearyl alcohol | Cetearyl alcohol |
| 1 | 5.0 | Kaolin clay | Kaolin |
| 4 | 4.0 | Sodium stearoyl lactylate | Sodium stearoyl lactylate |
| 4 | 2.0 | Glycerin | Glycerin |
| 4 | 1.0 | Cetyl hydroxyethyl-cellulose | Cetyl hydroxyethyl-cellulose |
| 4 | 5.0 | Keltrol (1%) | Water and Xathan gum |
| 4 | 3.0 | Caprylyl glycol | Caprylyl alcohol |
| 4 | 2.0 | Potassium sorbate | Potassium sorbate |
| 4 | 2.0 | Tocopheryl acetate | Tocopheryl acetate |
| 5 | qs | NaOH (18%) | Water and sodium hydroxide |

Formulation Procedure:
1. In a beaker, combine Sequence #2 ingredients, mix slightly for 10 minutes and set aside.
2. In another beaker, combine Sequence #3 ingredients, heat to 50° C., mix for 15 minutes.
3. In a main beaker, combine Sequence #1 ingredients, homogenize until smooth.
4. Add Sequence #4 ingredients into the main beaker, heat to 70° C., mix.
5. When batch temperature reaches 70° C., add Sequence #2 into the main beaker (which now has Sequence #1 and #4), continue to mix for 10 minutes.
6. Cool the main beaker down to 50° C., then add Sequence #3, mix for 10 minutes. Cool the main beaker down to 25° C.
7. Adjust the batch to pH 7.0-8.0 with Sequence #5.

Example 2

| \multicolumn{4}{c}{Preferred formulation for an eye cream} |

| Sequence | Percent | Ingredient | INCI Name |
|---|---|---|---|
| 1 | 36.0 | Deionized water | Water |
| 3 | 2.0 | Hemp oil | Hemp oil |
| 2 | 1.0 | Chinese foxglove extract | *Rehmannia chinesis* root extract |
| 2 | 1.0 | *Lilyturf* root | *Ophiopogon japonicus* root extract |
| 2 | 1.5 | *Panax ginseng* | *Panax ginseng* root extract |
| 2 | 0.5 | Dragon's blood resin | *Croton lechleri* resin extract |
| 2 | 1.0 | Goji berry extract | Hydrolyzed *Lycium barbarum* fruit extract |
| 2 | 2.0 | Shou Wu Chi extract | Radix *polygoni multiflori* extract |
| 2 | 1.0 | *Wu Wei Zi* extract | *Schisandrae chinensis* extract |
| 2 | 2.5 | *Astragalus* extract | *Astragalus membranaceus* root extract |
| 2 | 2.0 | *Peony* (white) | *Paeonia albiflora* extract |
| 3 | 2.0 | *Jojoba* oil unsaponifiables | *Jojoba* oil |
| 3 | 4.0 | *Sunflower* oil unsaponifiables | *Sunflower* oil |
| 1 | 8.5 | Candellila/*jojoba*/rice bran polyglyceryl-3-esters | Candellila/*jojoba*/rice bran polyglyceryl-3-esters |
| 1 | 8.0 | Glyceryl stearate | Glyceryl stearate |
| 1 | 6.0 | Cetearyl alcohol | Cetearyl alcohol |
| 1 | 4.0 | Sodium stearoyl lactylate | Sodium stearoyl lactylate |
| 1 | 1.0 | Sodium hyaluronic | Sodium hyaluronate |
| 1 | 2.0 | Glycerin | Glycerin |
| 1 | 1.0 | Cetyl hydroxyethyl-cellulose | Cetyl hydroxyethyl-cellulose |
| 1 | 5.0 | Keltrol (1%) | Water and Xanthan gum |
| 1 | 3.0 | Caprylyl glycol | Caprylyl alcohol |
| 1 | 2.0 | Potassium sorbate | Potassium sorbate |
| 1 | 2.0 | Tocopheryl acetate | Tocopheryl acetate |
| 4 | qs | NaOH (18%) | Water and sodium hydroxide |

Formulation Procedure:
1. In a beaker, combine Sequence #2 ingredients, mix slightly for 10 minutes and set aside.
2. In another beaker, combine Sequence #3 ingredients, heat to 50° C., mix for 15 minutes.
3. In a main beaker, combine Sequence #1 ingredients, heat to 70° C., mix.
4. When batch temperature reaches 70° C., add Sequence #2 into the main beaker (which now has Sequence #1), continue to mix for 10 minutes.
5. Cool the main beaker down to 50° C., then add Sequence #3, mix for 10 minutes. Cool the main beaker down to 25° C.
6. Adjust the batch to pH 6.8-8.0 with Sequence #5.

All references, including publications, patent applications, and patents, cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

I claim:
1. A dermal topical composition for treating human skin which has crow's feet, wrinkles, is sagging or has pigmentation due to age of the human consisting essentially of:
   (a) a dermatologically amount of *cannabis sativa* L. oil having a cannabinoid content of at least 10% (wt/wt), at between about 0.1% (wt/wt) and about 5% (wt/wt) of the composition;
   (b) about 0.1% to 2% of *Angelica sinensis* extract; about 0.1% to 3.5% *Croton lechleri* resin; about 01% to 2% of *Astragalus membranaceous* Root extract; and
   (c) an emulsifier, cosmetic fillers, builking agents, preservatives, or moisturizing agent selected from the group consisting of:
      about 3% (wt/wt) to about 15% (wt/wt) of candellia/jojoba/rice bran polyclyceryl-3-ester;
      about 2% (wt/wt) to about 15% (wt/wt) of glyceryl stearate;

about 2% (wt/wt) to about 10% (wt/wt) of cetearyl alcohol;

about 2% (wt/wt) to about 10% (wt/wt) of sodium stearoyl lactylate;

about 0.5% (wt/wt) to about 2% (wt/wt) of sodium hyaluronate;

about 1% (wt/wt) to about 5% (wt/wt) of glycerin;

about 0.5% (wt/wt) to about 5% (wt/wt) of cetyl hydroxyethylcellulose;

about 0.5% (wt/wt) to about 10% (wt/wt) of xathan gum;

about 1% (wt/wt) to about 5% (wt/wt) of caprylyl alcohol;

about 1% (wt/wt) to about 5% (wt/wt) of potassium sorbate; and about 1% (wt/wt) to about 5% (wt/wt) of tocopherol; and an effective amount of sodium hydroxide present to increase the pH level in the overall composition and to prevent the dragon's blood resin from turning a shade of pink, wherein a slightly basic or neutral pH environment prevents the composition from being abrasive to the skin.

2. The composition of claim 1, further consisting essentially of jojoba oil at between about 1% (wt/wt) and about 3% (wt/wt).

3. The composition of claim 1, further consisting essentially of a sufficient quantity of sodium hydroxide to bring the pH of the composition to between 6.8 and 8.

4. The composition of claim 1, further consisting essentially of water with up to 100% of the weight of the composition being water.

5. The composition of claim 2, further consisting essentially of bentonite clay at between about 1% (wt/wt) and about 8% (wt/wt).

6. The composition of claim 1, further consisting essentially of *Artemisia vulgaris* extract at between about 0.1% (wt/wt) and about 2% (wt/wt).

7. The composition of claim 1, further consisting essentially of *Glycyrrhiza glabra* extract at between about 0.1% (wt/wt) and about 2% (wt/wt).

8. The composition of claim 1, further consisting essentially of *Rosa canina* powder at between about 0.1% (wt/wt) and about 1% (wt/wt).

9. A composition according claim 1, wherein the composition is an eye-cream, a serum, a gel masque, a moisturizer, an exfoliant, or a cleanser.

10. A dermal topical composition for treating human skin which has crow's feet, wrinkles, is sagging or has pigmentation due to age of the human consisting essentially of:
 (a) a dermatologically amount of *cannabis sativa* L. oil having a cannabinoid content of at least 10% (wt/wt), at between about 0.1% (wt/wt) and about 5% (wt/wt) of the composition;
 (b) about 0.1% to 3.5% *Croton lechleri* resin;
  about 01% to 2% of *Astragalus membranaceous* Root extract;
  about 01% to 2% of *Lycium Barbarum* extract; and
 (c) an emulsifier, cosmetic fillers, builking agents, preservatives, or moisturizing agent selected from the group consisting of:
  about 3% (wt/wt) to about 15% (wt/wt) of candellia/jojoba/rice bran polyclyceryl-3-ester;
  about 2% (wt/wt) to about 15% (wt/wt) of glyceryl stearate;
  about 2% (wt/wt) to about 10% (wt/wt) of cetearyl alcohol;
  about 2% (wt/wt) to about 10% (wt/wt) of sodium stearoyl lactylate;
  about 0.5% (wt/wt) to about 2% (wt/wt) of sodium hyaluronate;
  about 1% (wt/wt) to about 5% (wt/wt) of glycerin;
  about 0.5% (wt/wt) to about 5% (wt/wt) of cetyl hydroxyethylcellulose;
  about 0.5% (wt/wt) to about 10% (wt/wt) of xathan gum;
  about 1% (wt/wt) to about 5% (wt/wt) of caprylyl alcohol;
  about 1% (wt/wt) to about 5% (wt/wt) of potassium sorbate; and
  about 1% (wt/wt) to about 5% (wt/wt) of tocopherol; and
 an effective amount of sodium hydroxide present to increase the pH level in the overall composition and to prevent the dragon's blood resin from turning a shade of pink, wherein a slightly basic or neutral pH environment prevents the composition from being abrasive to the skin.

11. The composition of claim 10, further consisting essentially of jojoba oil at between about 1% (wt/wt) and about 3% (wt/wt).

12. The composition of claim 10, further consisting essentially of a sufficient quantity of sodium hydroxide to bring the pH of the composition to between 6.8 and 8.

13. The composition of claim 10, further consisting essentially of water with up to 100% of the weight of the composition being water.

14. The composition of claim 12, further consisting essentially of bentonite clay at between about 1% (wt/wt) and about 8% (wt/wt).

15. The composition of claim 10, further consisting essentially of *Glycyrrhiza glabra* extract at between about 0.1% (wt/wt) and about 2% (wt/wt).

16. A composition according claim 10, wherein the composition is an eye-cream, a serum, a gel masque, a moisturizer, an exfoliant, or a cleanser.

17. A dermal topical composition for treating human skin which has crow's feet, wrinkles, is sagging or has pigmentation due to age of the human consisting essentially of:
 (a) a dermatologically amount of *cannabis sativa* L. oil having a cannabinoid content of at least 10% (wt/wt), at between about 0.1% (wt/wt) and about 5% (wt/wt) of the composition;
 (b) about 0.1% to 3.5% *Croton lechleri* resin;
  about 01% to 2% of *Astragalus membranaceous* Root extract; and
  about .1% to 3% of *Ligusticum wallichii* extract.
 (c) an emulsifier, cosmetic fillers, builking agents, preservative, or moisturizing agent selected from the group consisting of:
  about 3% (wt/wt) to about 15% (wt/wt) of candellia/jojoba/rice bran polyclyceryl-3-ester;
  about 2% (wt/wt) to about 15% (wt/wt) of glyceryl stearate;
  about 2% (wt/wt) to about 10% (wt/wt) of cetearyl alcohol;
  about 2% (wt/wt) to about 10% (wt/wt) of sodium stearoyl lactylate;
  about 0.5% (wt/wt) to about 2% (wt/wt) of sodium hyaluronate;
  about 1% (wt/wt) to about 5% (wt/wt) of glycerin;
  about 0.5% (wt/wt) to about 5% (wt/wt) of cetyl hydroxyethylcellulose;

about 0.5% (wt/wt) to about 10% (wt/wt) of xathan gum;

about 1% (wt/wt) to about 5% (wt/wt) of caprylyl alcohol;

about 1% (wt/wt) to about 5% (wt/wt) of potassium sorbate; and about 1% (wt/wt) to about 5% (wt/wt) of tocopherol; and an effective amount of sodium hydroxide present to increase the pH level in the overall composition and to prevent the dragon's blood resin from turning a shade of pink, wherein a slightly basic or neutral pH environment prevents the composition from being abrasive to the skin.

18. The composition of claim 17, further consisting essentially of *Ophiopogon japonicus* extract at between about 0.1% (wt/wt) and about 3% (wt/wt).

19. A composition according claim 17, wherein the composition is an eye-cream, a serum, a gel masque, a moisturizer, an exfoliant, or a cleanser.

* * * * *